US008399209B2

(12) United States Patent  
Schelp et al.

(10) Patent No.: US 8,399,209 B2  
(45) Date of Patent: Mar. 19, 2013

(54) HOMOGENEOUS DETECTION METHOD

(75) Inventors: Carsten Schelp, Hockessin, DE (US); Michael Trier, Wetter (DE); Hrair Kirakossian, San Jose, CA (US)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 537 days.

(21) Appl. No.: 11/443,270

(22) Filed: May 31, 2006

(65) Prior Publication Data

US 2007/0082346 A1  Apr. 12, 2007

Related U.S. Application Data

(63) Continuation of application No. PCT/EP2004/012648, filed on Nov. 9, 2004, which is a continuation of application No. 10/725,070, filed on Dec. 1, 2003, now abandoned.

(60) Provisional application No. 60/526,116, filed on Dec. 1, 2003.

(51) Int. Cl.  
*G01N 33/00* (2006.01)

(52) U.S. Cl. ............ 435/7.92; 435/7.93; 435/7.94; 436/501; 436/518

(58) Field of Classification Search .......... None  
See application file for complete search history.

(56) References Cited

U.S. PATENT DOCUMENTS

| | | | |
|---|---|---|---|
| 3,996,345 A | 12/1976 | Ullman et al. | |
| 4,228,237 A | 10/1980 | Hevey et al. | |
| 4,376,110 A * | 3/1983 | David et al. ............ | 435/5 |
| 4,434,150 A | 2/1984 | Azad et al. | |
| 4,448,908 A | 5/1984 | Pauly et al. | |
| 4,590,169 A | 5/1986 | Cragle et al. | |
| 4,595,661 A | 6/1986 | Cragle et al. | |
| 4,663,278 A | 5/1987 | DiNello | |
| 4,778,751 A | 10/1988 | El Shami et al. | |
| 4,918,004 A | 4/1990 | Schwartz | |
| 4,945,146 A | 7/1990 | Kapmeyer et al. | |
| 4,962,046 A | 10/1990 | Kapmeyer | |
| 5,151,954 A | 9/1992 | Takai | |
| 5,340,716 A | 8/1994 | Ullman et al. | |
| 5,362,655 A | 11/1994 | Schenk | |
| 5,420,016 A | 5/1995 | Boguslaski et al. | |
| 5,437,983 A | 8/1995 | Watts et al. | |
| 5,527,684 A | 6/1996 | Mabile et al. | |
| 5,545,834 A | 8/1996 | Singh et al. | |
| 5,641,629 A | 6/1997 | Pitner et al. | |
| 5,739,042 A * | 4/1998 | Frengen ............ | 436/523 |
| 5,858,803 A | 1/1999 | Schenk | |
| 5,914,230 A | 6/1999 | Liu et al. | |
| 5,981,180 A * | 11/1999 | Chandler et al. ........ | 435/6 |
| 6,187,594 B1 | 2/2001 | Kraus et al. | |
| 6,406,913 B1 | 6/2002 | Ullman et al. | |
| 6,610,494 B2 | 8/2003 | Marquardt et al. | |
| 2002/0081617 A1 * | 6/2002 | Buranda et al. ........ | 435/6 |
| 2002/0119497 A1 | 8/2002 | Wild et al. | |
| 2003/0003602 A1 | 1/2003 | Vogt et al. | |
| 2003/0175808 A1 | 9/2003 | Kurokawa et al. | |
| 2005/0202513 A1 | 9/2005 | Kitayama et al. | |
| 2010/0248218 A1 | 9/2010 | Schelp et al. | |

FOREIGN PATENT DOCUMENTS

| | | |
|---|---|---|
| CA | 2034922 A1 | 8/1991 |
| CA | 2193344 | 6/1997 |
| EP | 0070514 A2 | 1/1983 |
| EP | 0 080 614 A2 | 6/1983 |
| EP | 0 227 054 B1 | 7/1987 |
| EP | 0 245 926 A1 | 11/1987 |
| EP | 0 246 446 B1 | 11/1987 |
| EP | 0 263 401 B1 | 4/1988 |
| EP | 0 105 714 B1 | 7/1988 |
| EP | 0 315 364 A2 | 5/1989 |
| EP | 0 138 297 B1 | 8/1989 |
| EP | 0 411 945 A2 | 2/1991 |
| EP | 0 515 194 A2 | 11/1992 |
| EP | 0 516 529 A2 | 12/1992 |
| EP | 0 603 958 A1 | 6/1994 |
| EP | 0349988 B1 | 6/1994 |
| EP | 0 617 285 A2 | 9/1994 |
| EP | 0356964 B1 | 1/1995 |
| EP | 0444561 B1 | 11/1996 |
| EP | 0 781 998 A2 | 7/1997 |
| EP | 0 787 986 A1 | 8/1997 |
| JP | 7239331 A | 9/1995 |
| JP | 2000-346843 A | 12/2000 |
| JP | 2002-277464 A | 9/2002 |
| JP | 2002-335973 A | 11/2002 |
| JP | 2003-194817 A | 7/2003 |
| JP | 3426241 B | 9/2003 |
| JP | 2003-329686 A | 11/2003 |
| WO | WO 93/01498 | 1/1993 |
| WO | WO 95/06877 | 3/1995 |
| WO | WO 95/14928 A1 | 6/1995 |
| WO | WO 95/25172 | 9/1995 |
| WO | WO 98/15830 A1 | 4/1998 |

(Continued)

OTHER PUBLICATIONS

Diamandis et al., Immunoassay, Academic Press, Chapter 11, The Avidin-Biotin System, 1996, pp. 237-267.*  
Burarida et al., Peptides, Antibodies, and FRET on Beads in Flow Cytometry: A model System Using Fluoresceinated and Biotinylated B—Endorphin, Cytometry 37: 1999, pp. 21-31.*  
Vignali, "Multiplexed Particle-Based Flow Cytometric Assays," *Journal of Immunological Methods* 243:243-255 (2000).  
Böcher et al., "Synthesis of Mono- and Bifunctional Peptide—Dextran Conjugates for the Immobilization of Peptide Antigens on ELISA Plates: Properties and Application," *Journal of Immunological Methods*, 208:191-202 (1997).

(Continued)

*Primary Examiner* — Gary W Counts  
(74) *Attorney, Agent, or Firm* — Finnegan, Henderson, Farabow, Garrett & Dunner, LLP

(57) ABSTRACT

The invention relates to methods for the quantitative or qualitative detection of an analyte in an assay and adequate reagents therefor, particularly a homogeneous binding test. According to the invention, an analyte-specific binding partner R1 comprises more than one specific binding point for a specific binding partner X that is associated with a component of a signal-forming system while a second analyte-specific binding partner R2 comprises more than one specific binding point for a specific binding partner Y which is also associated with a component of a signal-forming system.

29 Claims, No Drawings

FOREIGN PATENT DOCUMENTS

| | | |
|---|---|---|
| WO | WO 03/044231 | 5/2003 |
| WO | WO 03/083486 A1 | 10/2003 |

OTHER PUBLICATIONS

Hämä et al., "Zeptomole Detection Sensitivity of Prostate-Specific Antigen in a Rapid Microlitre Plate Assay Using Time-Resolved Fluorescence," *Luminescence*, 15:351-355 (2000).

Hurskainen et al., "Heterogeneous and Homogeneous Time-Resolved Fluorescence-Based Assays for a Low-Affinity Binding Reaction," URL:http://las.perkinelmer.com/content/RelatedMaterials/ScientificPosters/S4168-TRFBasedAssaysforLow-AffinityBindingReaction.pdf, pp. 1-8 (2002).

PerkinElmer Life Sciences, "A Practical Guide to Working with AlphaScreen™," URL:http://las.perkinelmer.com/content/RelatedMaterials/S4077.pdf, pp. 1-47 (2003).

Ullman et al., "Luminescent Oxygen Channeling Assay (LOCI™): Sensitive, Broadly Applicable Homogeneous Immunoassay Method," *Clinical Chemistry* 42(9):1518-1526 (1996).

Papik, K., et al; "Automated Prozone Effect Detection in Ferritin Homogeneous Immunoassays Using Neural Network Classifiers;" *Clin Chem Lab Med*, 37(4), pp. 471-476 (1999).

Larrick, J. W., et al.; "Recombinant Antibodies;" *Hum. Antibod. Hybridomas*, vol. 2, pp. 172-189 (1991).

Messerschmid, S.; "Erzeugung Von Polyklonalen Antikörpern in Nicht-Säugern;" *BIOforum*, pp. 500-502 (1996).

Fischer, R., et al.; "Molecular Farming of Recombinant Antibodies in Plants;" *Biol. Chem.*, vol. 380, pp. 825-839 (1999).

Hiatt, A., et al.; "Assembly of Antibodies and Mutagenized Variants in Transgenic Plants and Plant Cell Cultures;" *Genetic Engineering*, vol. 14, pp. 49-64 (1992).

Bailey, M. P., et al.; "On the Use of Fluorescent Labels in Immunoassay;" *Journal of Pharmaceutical & Biomedical Analysis*, vol. 5, No. 7, pp. 649-658 (1987).

Udenfriend, S., et al.; "Scintillation Proximity Radioimmunoassay Utilizing $^{125}$I-labeled Ligands;" *Proc. Natl. Acad. Sci*, USA, vol. 82, pp. 8672-8676 (1985).

Mathis, G.; "Rare Earth Cryptates and Homogeneous Fluoroimmunoassays With Human Sera;" *Clin. Chem*, vol. 39, No. 9, pp. 1953-1959 (1993).

Boguslaski, R. C., et al.; "Homogeneous Immunoassays;" *Applied Biochemistry and Biotechnology*, vol. 7, pp. 401-414 (1982).

Ullman, E. F., et al.; "Luminescent Oxygen Channeling Immunoassay: Measurement of Particle Binding Kinetics by Chemiluminescence;" *Proc. Natl. Acad. Sci*, USA, vol. 91, pp. 5426-5430 (1994).

Eriksson, S., et al.; "Dual-Label Time-Resolved Immunofluorometric Assay of Free and Total Prostate-Specific Antigen Based on Recombinant Fab Fragments;" *Clinical Chemistry*, vol. 46, No. 5, pp. 658-666 (2000).

U.S. Appl. No. 11/443,301, filed May 31, 2006 by Schelp et al.: Non-Final Office Action, dated Feb. 17, 2010.

U.S. Appl. No. 11/443,301, filed May 31, 2006 by Schelp et al.: Final Office Action, dated Oct. 13, 2010.

\* cited by examiner

HOMOGENEOUS DETECTION METHOD

This is a continuation of PCT International Application No. PCT/EP2004/012648, filed Nov. 9, 2004, which is a continuation application of U.S. patent application Ser. No. 10/725,070, filed Dec. 1, 2003, now abandoned, and claims the benefit of U.S. Provisional Application No. 60/526,116, filed Dec. 1, 2003, all of which are incorporated herein by reference.

The invention relates to methods for quantitatively or qualitatively detecting an analyte in a sample and to suitable reagents for this purpose.

For the purpose of detecting analytes, use is frequently made of binding tests in which the specific binding of analyte to be detected to analyte-specific binding partners makes it possible to draw conclusions as to the presence, absence or quantity of the analyte in a sample. Immunoassays or methods in which oligonucleotides or polynucleotides are hybridized are examples of binding tests.

What are termed the "heterogeneous binding tests" are characterized by one or more separation steps and/or washing steps. The separation can be effected, for example, by immunoprecipitation, precipitation with substances such as polyethylene glycol or ammonium sulfate, filtration, magnetic separation or binding to a solid phase. Such a "solid phase" consists of porous and/or nonporous material which is as a rule insoluble in water. It can have a very wide variety of forms such as: a vessel, a small tube, a microtitration plate, a sphere, a microparticle, a rod or a strip, or filter paper or chromatography paper, etc. In the case of heterogeneous binding tests in sandwich format, one of the analyte-specific binding partners is as a rule bound to a solid phase and is used for separating off the "analyte/analyte-specific binding partner" binding complex from the liquid phase while the other analyte-specific binding partner carries a detectable label (e.g. an enzyme, a fluorescent label or a chemiluminescent label, etc.) for the purpose of detecting the binding complex. These test methods are further subdivided into what are termed single-step sandwich tests, in which the two specific binding partners are incubated simultaneously with the sample, and into two-step sandwich tests, in which the sample is first of all incubated with the solid phase reagent and, after a separation and washing step, the solid phase-bound binding complex, consisting of analyte and analyte-specific binding partner, is incubated with the detection reagent.

In "homogeneous binding tests", no separation takes place between free components of the signal-generating system and components of the system which are bound to the "analyte/analyte-specific binding partner" complex. The test mixture, which contains the analyte-specific binding partners, the signal-forming components and the sample, is measured after, or even during, the binding reaction without any further separation and/or washing step and the corresponding measurement signal is determined. Examples of homogeneous immunoassays (see also Boguslaski & Li (1982) Applied Biochemistry and Biotechnology, 7: 401-414) are many turbidimetric or nephelometric methods, with it being possible for the analyte-specific binding partners, which are used for the detection, to be associated with latex particles; EMIT® tests; CEDIA® tests; Fluorescent-Polarization Immunoassays; Luminescent Oxygen Channeling Immunoassays ("LOCI", see EP-A2-0 515 194; Ullman et al. (1994) Proc. Natl. Acad. Sci., 91: 5426-5430; Ullman et al., (1996) Clinical Chemistry, 42: 1518-1526); etc. In a homogeneous sandwich immunoassay, such as a nephelometric latex test, the antibody reagents are incubated together with the sample and the signal is measured during and/or after the incubation without any separation or washing step being carried out prior to the measurement. Expressed in other words: the antibody-bound analyte is not separated from the free analyte or from antibodies which have not bound any analyte.

Homogeneous and heterogeneous binding tests can also be carried out in the form of what is termed a "sandwich assay". In this case, the analyte is, for example in a heterogeneous binding test, bound by a solid phase-associated analyte-specific binding partner and an analyte-specific binding partner which is associated with a component of a signal-generating system. In sandwich immunoassays, antibodies or antigens or haptens can be the analyte-specific binding partners.

The "indirect immunoassay" is another special embodiment of a heterogeneous or homogeneous binding test. In this case, the analyte is an antibody. One of the analyte-specific binding partners is the antigen, or a modified antigen, of the antibody (=analyte) to be detected and the other analyte-specific binding partner is as a rule an immunoglobulin-binding protein, such as an antibody which is able to specifically bind the antibody (=analyte) to be detected.

In a homogeneous or heterogeneous "competitive binding test", sample analyte and reagent analyte (for example a "modified analyte" such as a labeled analyte, analyte fragment or analyte analog) compete for binding to a limited number of analyte-specific binding partners. Examples for illustrating the principle: (i) sample analyte competes with reagent analyte, which is associated with a component of a signal-generating system, for binding to solid phase-associated analyte-specific binding partners or (ii) sample analyte competes with solid phase-associated analyte (=reagent analyte) for binding to analyte-specific binding partners which are associated with a component of a signal-generating system.

However, in the case of many binding tests, great difficulties arise when preparing the reagents since the binding of the analyte-specific binding partners to solid phases or particulate components of a signal-generating system (e.g. microparticles) frequently causes the analyte-specific binding partners which have been bound in this way to loose activity and/or gives rise to changes in the properties (e.g. as regards conformation or stability) of these binding partners. This applies, in particular, when the analyte-specific binding partners which have been bound are proteins, such as antibodies or enzymes.

Attempts have therefore been made to remedy this problem by introducing what are termed "universal reagents" (see, e.g., EP-0 105 714). Thus, according to EP-0 245 926, it is possible to detect an analyte by using, as a universal solid-phase reagent, an avidin-coated solid phase to which the biotinylated analyte-specific binding partner is bound. Other methods use a biotinylated analyte-specific binding partner which is able, for example, to bind to a streptavidin/enzyme complex which is used as a universal detection reagent. However, in these tests, separation steps, such as washing steps, are an essential element in carrying out the test.

Particular difficulties in regard to using universal reagents arise in homogeneous binding tests, particularly in homogeneous binding tests which are based on using particulate universal reagents (e.g. streptavidin-coated microparticles). If the analyte-specific binding partner were divalent or polyvalent, i.e. possessed two or more binding sites for the particulate universal reagents (e.g. if it were an antibody to which two or more biotin molecules were bound), this would then lead to the microparticle being agglutinated even without an analyte being present in the sample. This would then result in erroneous determinations. According to EP-0 356 964, EP-0 349 988 and EP 0 444 561, it is therefore regarded as being essential for being able to carry out such a homogeneous test that the analyte-specific binding partner is monovalent in regard to the universal reagent, i.e. that the binding partner only possesses one binding site for the universal reagent (e.g. streptavidin-latex particle). In the case of homogeneous LOCI tests as well (see EP-0 515 194), the inventors point out that the generation of a measurement signal depends on the formation of particle pairs which in each case consist of one sensitizer particle and one chemiluminescer particle (Ullman et al., (1996) Clinical Chemistry, 42: 1518-1526). A disadvantage of these methods is that the number of binding sites on the corresponding analyte-specific binding partner has to be controlled precisely.

EP-0 138 297 takes another approach. In this case, the number of biotinylated antibodies which are to bind to avidin-coated latex particles is controlled by it being necessary to add free biotin. However, a measure of this nature has a negative effect both on reagent stability and on the analytical sensitivity of the test. Furthermore, the universal reagent in this case reacts with the corresponding analyte-specific binding partner prior to the actual test method, i.e. the antibodies which are bound to the latex particles by way of a biotin/avidin bridge constitute the reagent which is to be employed in the test. This suffers from the disadvantage that the universal reagent cannot be used on the analytical unit with different analyte-specific binding partners depending on the test which is to be carried out.

The object was therefore to develop an improved method for detecting an analyte, in particular using homogeneous test procedures, with this method not exhibiting the above-described disadvantages. A method of this nature can be used particularly advantageously in automated analytical equipment.

This object is achieved by providing the novel method and materials which are described in the claims.

The novel method achieves this object by making available universal reagents (specific binding partners X or Y, each of which is associated with a component of a signal-generating system), which can be adjusted independently of the analyte-specific reagents (analyte-specific binding partners R1 and R2) to the specific interests, and enabling analytes to be detected with a high degree of sensitivity and precision.

Since the analyte-specific binding partners of the signal-generating components can be used independently of each other and since the analyte-specific binding partners and the signal-generating components can be optimally adjusted, independently of each other, to the given requirements, this invention also solves the following general problem of homogeneous binding tests, namely the mutually opposed requirements for optimal differentiation and optimal sensitivity: the concentration of the reagents should, on the one hand, be limited so as to ensure that the background signals are as low as possible and, on the other hand, the reagents should be highly concentrated and highly labeled in order to achieve a satisfactory change in signal per unit of time.

The analyte-specific, novel binding partners R1 and/or R2 are characterized by the fact that they exhibit more than one binding site for the respective specific binding partner X or Y which is associated with components of a signal-generating system. Preference is given, in the novel method, to using universal reagents which comprise components of a signal-generating system which can interact with each other, e.g. in the form of an energy transfer, over very short distances.

It has been found, surprisingly, that the novel use, in homogeneous test methods, of analyte-specific binding partners which possess more than one binding site for the given universal reagent does not lead to erroneous measurements but, on the contrary, to what is even an improvement in the ratio of background signal to analyte-specific measurement signal (see, e.g., Tables 3 and 4).

Since the binding sites of the analyte-specific binding partners for the given universal reagents preferably consist of small molecules, e.g. haptens such as digoxigenin, biotin, DNP or FITC, which are preferably bonded covalently to the analyte-specific binding partners, the analyte-specific activity or binding capacity of R1 or R2 is as a rule not impaired or hardly impaired. The binding sites can also be part of the unaltered analyte-specific binding partner. Thus, the analyte-specific binding partner could, for example, be a human IgG antibody which possesses several binding sites which are specifically recognized by anti-human IgG antibodies from another species.

The invention preferably relates, in one instance, to a homogeneous method for quantitatively or qualitatively detecting an analyte in a sample, with the analyte-specific binding partner R1 possessing specific binding sites for the specific binding partner X, which is associated with a component of a signal-generating system, and the analyte-specific binding partner R2 possessing specific binding sites for the specific binding partner Y, which is associated with a component of a signal-generating system, which comprises R1 and/or R2 possessing more than one binding site for the respective specific binding partner which is associated with components of a signal-generating system. A particular advantage of the invention is that the specific binding partners X and/or Y (e.g. avidin, streptavidin, etc.) do not, as described in EP-0 138 297, have to be saturated by adding free "specific binding sites" (e.g. biotin).

This novel method is particularly preferably a homogeneous binding test, in particular a homogeneous immunoassay. As already explained above, this homogeneous binding test can be carried out, inter alia, in the form of a sandwich assay, an indirect immunoassay or a competitive binding test.

Some terms which have been used for describing the invention are explained in more detail below:

A "quantitative detection" measures the quantity, concentration or activity of the analyte in the sample. The term "quantitative detection" also encompasses semiquantitative methods which only record the approximate quantity, concentration or activity of the analyte in the sample or can only be used to give an indication of the relative quantity, concentration or activity. A "qualitative detection" is to be understood as meaning simply detecting whether the analyte or its activity is present or absent in the sample or indicating that the quantity, concentration or activity of the analyte in the sample is below or above one specific threshold value or several specific threshold values.

The term "analyte" is to be understood as meaning the substance which is to be detected in the novel method. Examples of an analyte are listed on pages 8-15 in EP-A2-0 515 194. The analyte can be a member of a specific binding pair. The analyte may possess one binding site (monovalent, usually a hapten) or several binding sites (polyvalent). In immunochemical tests, such a binding site is frequently also termed an epitope. In addition, the analyte can be a single substance or a group of substances which possess at least one single shared binding site.

A monovalent analyte generally has a molecular weight of from about 100 to 2000, in particular of from 125 to 1000. Many oligopeptides, oligonucleotides, oligosaccharides, pharmaceuticals, drugs, metabolites, pesticides, etc. are covered by the term monovalent analyte. A polyvalent analyte generally has a molecular weight of more than 2000, usually more than 10,000. Examples of polyvalent analytes are polypeptides, polysaccharides, nucleic acids, cells, cell constituents, including chromosomes, genes, mitochondria and other cell organelles, cell membranes, etc. Proteins are frequently the substances which are to be detected. These proteins may be members of a protein family which are characterized by similar structural features and/or a similar biological function. Examples of analytically interesting protein families are pathogen proteins, immunoglobulins, cytokines, enzymes, hormones, tumor markers, metabolic markers, tissue-specific antigens, histones, albumins, globulins, scleroproteins, phospho-proteins, mucines, chromoproteins, lipoproteins, nucleoproteins, glycoproteins, proteoglycans, receptors, HLA, coagulation factors, cardiac infarction markers (e.g. myoglobin, troponin, pro-BNP, etc.), etc. Examples of other analytically interesting substances are single-stranded or double-stranded oligonucleotides and polynucleotides.

Within the meaning of the invention, a "sample" is to be understood as being the material which is suspected of containing the substance ("analyte") to be detected. For example, the term sample encompasses biological fluids or tissue which is derived, in particular, from humans or animals, such as blood, plasma, serum, sputum, exudate, bronchoalveolar lavage, lymph fluid, synovial fluid, seminal fluid, vaginal mucus, feces, urine, spinal fluid, hair, skin and tissue samples or tissue sections. The term also comprises cell culture samples, plant fluids or tissues, forensic samples, water and sewage samples, foodstuffs and pharmaceuticals.

In addition, the term "sample" also encompasses a pretreated sample which may contain the substance ("analyte") to be detected in a form in which it is released from carrier substances or is amplified: a number of samples have to be pretreated in order to make the analyte available for the detection method or in order to remove sample constituents which interfere. Such pretreatment of samples may involve the separation and/or lysis of cells, the precipitation, the hydrolysis or the denaturation of sample constituents such as proteins, centrifugation of samples, treatment of the sample with organic solvents such as alcohols, in particular methanol; or treatment of the sample with detergents. The sample is frequently transferred into another, usually aqueous, medium which is intended to interfere as little as possible with the detection method. The analyte may also be amplified. Amplification of nucleic acids leads, for example, to the generation of one or more copies of the nucleic acid chain to be detected. Such amplification methods, e.g. the polymerase chain reaction (PCR), the ligase chain reaction (LCR), amplification using Q beta replicase, nucleic acid sequence-based amplification (NASBA), single primer amplification (ASPP), and others, are well known to the skilled person.

An "analyte-specific binding partner" is to be understood as being either a specific binding partner which is able to bind specifically to the analyte or a specific binding partner (e.g. a modified analyte) which is able to bind to another analyte-specific binding partner. As a rule, a "modified analyte" is a substance which is at least able to bind to an analyte-specific binding partner but which differs from the sample analyte in lacking, or possessing additional, binding sites, e.g. a biotinylated analyte or an analyte which is associated with a component of a signal-generating system. A modified analyte is used, for example, in competitive tests.

A "specific binding partner" is to be understood as being a member of a specific binding pair. The members of a specific binding pair are two molecules each of which possesses at least one structure which is complementary to a structure possessed by the other molecule, with the two molecules being able to bind together specifically by way of a bond between the complementary structures. In this connection, the term molecule also encompasses molecular complexes such as enzymes which consist of an apoenzyme and a coenzyme, proteins which consist of several subunits, lipoproteins which consist of protein and lipids, etc. Specific binding partners can be naturally occurring substances or else substances which are prepared, for example, by means of chemical synthesis, microbiological techniques and/or recombinant DNA methods. Thus, it is by now possible to select specific binding partners using phage display libraries, synthetic peptide databases or recombinatorial antibody libraries (Larrick & Fry (1991) Human Antibodies and Hybridomas, 2: 172-189). The following may be mentioned as examples for the purpose of illustrating the term specific binding partner, without this being understood as any restriction: thyroxin-binding globulin, steroid-binding proteins, antibodies, antigens, haptens, enzymes, lectins, nucleic acids, repressors, oligonucleotides, polynucleotides, protein A, protein G, avidin, streptavidin, biotin, complement component C1q, nucleic acid-binding proteins, etc. Examples of specific binding pairs are: antibody-antigen, antibody-hapten, digoxigen/anti-digoxigen antibody, fluorescein/anti-fluorescein antibody, operator-repressor, nuclease-nucleotide, biotin-avidin, biotin/streptavidin, lectin-polysaccharide, steroid-steroid-binding protein, active compound-active compound receptor, hormone-hormone receptor, enzyme-substrate, IgG-protein A, complementary oligonucleotides or polynucleotides, etc. In what are termed homogeneous gene probe tests, the specific binding partners are as a rule nucleic acid chains which are at least in part complementary to segments of the nucleic acid chain which is to be detected.

Within the meaning of this invention, the term "antibody" is to be understood as signifying an immunoglobulin, e.g. an immunoglobulin of the class or subclass IgA, IgD, IgE, $IgG_1$, $IgG_{2a}$, $IgG_{2b}$, $IgG_3$, $IgG_4$ or IgM. An antibody possesses at least one binding site (frequently termed a paratope) for an epitope (frequently also termed antigenic determinant) on an antigen or hapten. Such an epitope is characterized, for example, by its spatial structure and/or by the presence of polar and/or apolar groups. The binding site possessed by the antibody is complementary to the epitope. The antigen-antibody reaction or the hapten-antibody reaction functions in accordance with what is termed the "key-lock principle" and is as a rule highly specific, i.e. the antibodies are able to distinguish between slight differences in the primary structure, in the charge, in the spatial configuration and in the steric arrangement of the antigen or hapten. What are termed the complementarity determining regions possessed by the antibody make a particular contribution to binding the antibody to the antigen or hapten.

The term "antigens" encompasses monovalent and polyvalent antigens. A polyvalent antigen is a molecule or a molecule complex to which more than one immunoglobulin can bind simultaneously whereas only one single antibody can bind at any one time to a monovalent antigen. A molecule which is not immunogenic on its own, but which is usually bound to a carrier for immunization purposes, is generally termed a hapten.

Within the meaning of this invention, the term antibody is not only to be understood as signifying complete antibodies but also, expressly, antibody fragments such as Fab, Fv, $F(ab')_2$ and Fab'; and also chimeric, humanized, bispecific, oligospecific or single-chain antibodies; and, furthermore, also aggregates, polymers and conjugates of immunoglobulins and/or their fragments provided the properties of binding to antigen or hapten are retained. Antibody fragments can be prepared, for example, by enzymatically cleaving antibodies using enzymes such as pepsin or papain. Antibody aggregates, antibody polymers and antibody conjugates can be generated using a wide variety of methods, e.g. by heat treatment, by reaction with substances such as glutaraldehyde, by reaction with immunoglobulin-binding molecules, by biotinylating antibodies and subsequently reacting them with streptavidin or avidin, etc.

Within the meaning of this invention, an antibody can be a monoclonal antibody or a polyclonal antibody. The antibody can have been prepared using the customary methods, e.g. by immunizing the human or an animal, such as a mouse, rat, guinea pig, rabbit, camel, horse, sheep, goat or chick (see also Messerschm id (1996) BIOforum, 11: 500-502), and subsequently isolating antiserum; or else by establishing hybridoma cells and subsequently purifying the secreted antibodies; or else by cloning and expressing the nucleotide sequences, or modified versions thereof, which encode the amino acid sequences which are responsible for binding the natural antibody to the antigen and/or hapten. Recombinant DNA methods can also be used, where appropriate, to prepare antibodies in plant, such as yeast cells (Fischer et al. (1999) Biol. Chem., 380: 825-839; Hiatt et. al. (1992) Genetic Engineering, 14, 49-64)), animal cells, prokaryotic cells (see, e.g., WO 95/25172) and isolated human cells.

A "signal-generating system" can consist of one or more components, with at least one of the components being a detectable label. A label is to be understood as being any molecule which itself produces a signal or which can induce the production of a signal, such as a fluorescent substance, a radioactive substance, an enzyme or a chemiluminescent substance. The signal can be detected or measured, for example, using the enzyme activity, the luminescence, the light absorption, the light scattering, the emitted electromagnetic or radioactive radiation, or a chemical reaction.

A "label" is able itself to generate a detectable signal such that no further components are required. Many organic molecules absorb ultraviolet and visible light, with these molecules being able to come into an excited energy state, as a result of the energy transferred by the absorption of the light, and emitting the absorbed energy in the form of light of a wavelength which is different from that of the incident light. Yet again other labels, such as radioactive isotopes, dyes or magnetic and nonmagnetic microparticles, are able to directly generate a detectable signal.

Yet again other labels require further components in order to generate the signal, i.e., in such a case, the signal-producing system includes all the components, such as substrates, coenzymes, quenchers, accelerators, additional enzymes, substances which react with enzyme products, catalysts, activators, cofactors, inhibitors, ions, etc., which are required for generating a signal.

Examples of suitable labels (see also EP-A2-0 515 194; U.S. Pat. No. 5,340,716; U.S. Pat. No. 5,545,834; Bailey et al. (1987) J. Pharmaceutical & Biomedical Analysis 5: 649-658) are enzymes, including horse radish peroxidase, alkaline phosphatase, glucose-6-phosphate dehydrogenase, alcohol dehydrogenase, glucose oxidase, β-galactosidase, luciferase, urease and acetylcholinesterase; dyes; fluorescent substances, including fluorescein isothio-cyanate, rhodamine, phycoerythrin, phycocyanin, ethidium bromide, 5-dimethy-laminonaphthalene-1-sulfonyl chloride and fluorescent chelates of rare earths; chemiluminescent substances, including luminol, isoluminol, acridinium compounds, olefin, enol ethers, enamine, arylvinyl ethers, dioxene, arylimidazole, lucigenin, luciferin and aequorin; sensitizers, including eosin, 9.10-dibromoanthracene, methylene blue, porphyrin, phthalocyanin, chlorophyll and rose Bengal; coenzymes; enzyme substrates; radioactive isotopes, including $^{125}$I, $^{131}$I, $^{14}$C, $^{3}$H, $^{32}$P, $^{35}$S, $^{14}$C, $^{51}$Cr, $^{59}$Fe, $^{57}$Co and $^{75}$Se; particles, including magnetic particles or particles, preferably latex particles, which can themselves be labeled, for example with dyes, sensitizers, fluorescent substances, chemiluminescent substances, isotopes or other detectable labels; sol particles, including gold sols or silver sols; liposomes or cells which can themselves be labeled with detectable labels; etc.

A signal-generating system can also comprise components which, when spatially close to each other, are able to enter into a detectable interaction, for example in the form of energy donors and energy recipients such as photosensitizers and chemiluminescent substances (EP-A2-0 515 194), photosensitizers and fluorophores (WO 95/06877), radioactive iodine$^{125}$ and fluorophores (Udenfriend et al. (1985) Proc. Natl. Acad. Sci. 82: 8672-8676), fluorophores and fluorophores (Mathis (1993) Clin. Chem. 39: 1953-1959) or fluorophores and fluorescent quenchers (U.S. Pat. No. 3,996,345).

An interaction between the components includes the direct transfer of energy between the components, for example as the result of light or electron radiation and also by way of short-lived reactive chemical molecules. In addition, it also includes processes in which the activity of one component is inhibited or augmented by one or more other components, for example an inhibition in or increase of the enzyme activity or an inhibition, increase or change (e.g. wavelength shift, polarization) in/of the electromagnetic radiation which is emitted by the affected component. Interaction between the components also includes enzyme cascades. In this case, the components are enzymes, at least one of which supplies the substrate for another enzyme, thereby resulting in the coupled substrate reaction having a maximal or minimal rate.

As a rule, an efficient interaction between the components takes place when these components are spatially adjacent, that is, for example, within a distance range of a few μm, in particular within a distance range of less than 600 nm, preferably less than 400 nm, very particularly preferably less than 200 nm.

In a very particularly preferred method according to the invention, the signal-generating system comprises microparticle-associated photosensitizers and microparticle-associated chemiluminescent substances.

Microparticles are frequently used as a solid phase and/or as a label. Within the meaning of this invention, the term "microparticles" is to be understood as signifying particles which have an approximate diameter of at least 20 nm and not more than 20 μm, generally between 40 nm and 10 μm, preferably between 0.1 and 10 μm, particularly preferably between 0.1 and 5 μm, very particularly preferably between 0.15 and 2 μm. The microparticles can have a regular or irregular shape. They can be spheres, spheroids or spheres possessing cavities or pores of greater or lesser size. The microparticles can consist of organic material or inorganic material or of a mixture or combination of both materials. They can consist of a porous or nonporous material and of a swellable or nonswellable material. While the microparticles can in principle be of any density, preference is given to particles which are of a density which approximates that of water, such as from about 0.7 to about 1.5 g/ml. The preferred microparticles can be suspended in aqueous solutions and are stable in suspension for as long as possible. They may be transparent, partially transparent or nontransparent. The microparticles can consist of several layers, such as what are termed core and shell particles, having a core and one or more enveloping layers. The term microparticles encompasses, for example, dye crystals, metal sols, silica particles, glass particles, magnetic particles, polymer particles, oil drops, lipid particles, dextran and protein aggregates. Preferred microparticles are particles which can be suspended in aqueous solutions and which consist of water-insoluble polymer material, particularly substituted polyethylenes. Very particular preference is given to latex particles, for example composed of polystyrene, acrylic acid polymers, methacrylic acid polymers, acrylonitrile polymers, acrylonitrile-butadiene-styrene, polyvinyl acetate-acrylate, polyvinylpyridine or vinyl chloride-acrylate. Latex particles which posses reactive groups, such as carboxyl, amino or aldehyde groups, on their surface, with these groups enabling specific binding partners, for example, to bind covalently to the latex particles, are of particular interest. The preparation of latex particles is described, for example, in EP 0 080 614, EP 0 227 054 and EP 0 246 446.

The term "associated" is to be understood broadly and comprises, for example, a covalent bond and a noncovalent bond, a direct bond and an indirect bond, absorption to a surface and enclosure in an invagination or a cavity, etc. In the case of a covalent bond, the specific binding partner is, for example, bonded to a label by way of a chemical bond. A covalent bond is usually said to exist between two molecules when at least one atomic nucleus in the first molecule shares electrons with at least one atomic nucleus in the second molecule. Examples of a noncovalent bond are surface adsorption, enclosure in cavities or the binding of two specific binding partners. In addition to direct binding to a label, the specific binding partners can also be bonded to the label indirectly by way of specific interaction with other specific binding partners. This will be illustrated by way of an example: a biotinylated anti-fluorescein antibody can be bound to the label by way of label-bound avidin.

A microparticle can posses a coating consisting of one or more layers, for example composed of proteins, carbohydrates, biopolymers, organic polymers, or mixtures thereof, in order, for example, to suppress or prevent the nonspecific binding of sample constituents to the particle surface or in order, for example, to achieve improvements in regard to suspension stability, stability during storage, conformational stability or resistance to UV light, microbes or other agents having a destructive effect. Thus, this coating can, in particular, consist of protein layers or polymer layers, such as cyclodextrans, dextrans, hydrogels, albumin or polyalbumins, which have been applied covalently or adsorptively to the microparticles.

In the inventive method, R1 and/or R2 can be bound to components of the signal-generating system by way of X and/or Y before, during or after the binding reaction with the analyte. The sample can be initially incubated with the analyte-specific binding partners R1 and R2, with the specific binding partners X and Y then being added subsequently. However, the reagents can also be added in another sequence.

When implementing a particularly preferred embodiment of the novel homogeneous binding test, the sample is first of all mixed sequentially or simultaneously with the analyte-specific binding partners R1 and R2 and, after that, the components of the signal-generating system, together with the binding partners X and Y, are added sequentially or simultaneously to the mixture.

The number of binding sites which the novel analyte-specific binding partner R1 possesses for the specific binding partner X should be at least 2, preferably at least 5, particularly preferably at least 10 and very particularly preferably at least 15, and the number of binding sites which the novel analyte-specific binding partner R2 possesses for the specific binding partner Y should be at least 2, preferably at least 5, particularly preferably at least 10 and very particularly preferably at least 15.

The novel analyte-specific binding partners R1 and R2 can also be one and the same analyte-specific binding partner or be different analyte-specific binding partners. Thus, in a sandwich immunoassay, for example, a monoclonal antibody can be used both as analyte-specific binding partner R1 and as analyte-specific binding partner R2 if the analyte possesses more than one epitope for this antibody.

In the novel method, the analyte-specific binding partners R1 and R2 are both able, in the case of a sandwich assay or of an indirect immunoassay, to bind the analyte specifically. In the case of a sandwich immunoassay, for example, the analyte-specific binding partners can be analyte-specific antibodies or, if the analyte is itself an antibody, be its antigen or a "modified antigen" or an antigen analog. In a competitive test set-up, one of the novel analyte-specific binding partners R1 and R2 should be a modified analyte.

The binding sites which the novel analyte-specific binding partner R1 possesses for the specific binding partner X are preferably haptens. Binding sites which are possessed by the novel analyte-specific binding partner R1 are particularly preferably biotin, digoxigenin, fluorescein, single-stranded nucleic acid chains or dinitrophenol. However, it is also possible to use other molecules which are in each case a member of a specific binding pair.

The binding sites which the novel analyte-specific binding partner R2 possesses for the specific binding partner Y are preferably haptens. The binding sites possessed by the novel analyte-specific binding partner R2 are particularly preferably biotin, digoxigenin, fluorescein, single-stranded nucleic acid chains or dinitrophenol. However, it is also possible to use other molecules which are in each case a member of a specific binding pair.

The novel specific binding partners X and Y can be one and the same specific binding partner or different specific binding partners. The novel specific binding partner X is preferably avidin, streptavidin, an anti-digoxigenin antibody, an anti-dinitrophenol antibody, a single-stranded nucleic acid chain or an anti-hapten antibody. However, it can also be an enzyme, an enzyme substrate or an antibody which is able to bind particular polypeptides, oligopeptides or enzymes specifically. The novel specific binding partner Y can also be avidin, streptavidin, an anti-digoxigenin antibody, an anti-dinitrophenol antibody, a single-stranded nucleic acid chain or an anti-hapten antibody. However, it can also be an enzyme, an enzyme substrate or an antibody which is able to bind particular polypeptides, oligopeptides or enzymes specifically.

In a particularly preferred embodiment of the novel method, components of the signal-generating system are brought, as a result of the analyte being bound to R1 and/or R2, to a distance from each other which permits an interaction, in particular an energy transfer, between these components. The magnitude of this interaction is then measured for the purpose of quantitatively or qualitatively detecting the analyte in the sample. This method is particularly suitable for sandwich assays and indirect immunoassays.

In another particularly preferred embodiment of the novel method, components of the signal-generating system are brought, as a result of the analyte being bound to R1 or R2, to a distance from each other which permits no interaction, or only a very slight interaction, in particular no energy transfer or only very slight energy transfer, between these components. The residual magnitude of this interaction is then measured for the purpose of quantitatively or qualitatively detecting the analyte in the sample. This method is particularly suitable for competitive binding tests.

In order to be able to increase the number of binding sites which the analyte-specific binding partners possess for the specific binding partners X or Y, without decreasing the specificity or sensitivity of the analyte-specific binding partners, it is possible to introduce carrier molecules to which both the analyte-specific binding partners and the binding sites can be bound. It is therefore advantageous, in the novel method, if R1 is one or more analyte-specific binding partners which is/are associated with a carrier molecule, with the carrier molecule being able to possess binding sites for the specific binding partner X. It is furthermore advantageous if R2 is also one or more analyte-specific binding partners which is/are associated with a carrier molecule, with the carrier molecule being able to possess binding sites for the specific binding partner Y.

In a particularly preferred embodiment according to the invention, R1 and/or R2 is/are in each case associated with such a carrier molecule. Examples of suitable carrier molecules are proteins, for example antibodies, enzymes, albumins, such as bovine serum albumin or human serum albumin, or protein polymers, dextrans, cyclodextrins, dendrimers or similar structures. Particularly preferred protein polymers or protein aggregates can consist of antibodies, albumin molecules, enzymes, or mixtures thereof, which are associated with each other and are preferably covalently bonded. Very particular preference is given to using biotinylated dextran and biotinylated protein polymers (e.g. biotinylated antibody polymers) as carrier molecules.

A particularly preferred carrier molecule can be prepared as described in Example 7. In this case, murine antibodies, preferably murine IgG antibodies, are covalently bonded to each other using a coupling reagent. Carrier molecules according to the invention can also be prepared in an analogous manner from enzymes, antibodies (e.g. mouse or goat antibodies, in particular IgG antibodies), albumins or mixtures thereof. The sites for binding the specific binding partner X or Y, e.g. biotin, digoxigenin, fluorescein, single-stranded nucleic acid chains, dinitrophenol, etc., can be bonded to these protein polymers using methods which are known to the skilled person, with a covalent bond being preferred.

An analyte-specific binding partner which is associated with a carrier molecule can, for example, be prepared as follows: the analyte-specific binding partner, preferably an antibody, particularly preferably an antibody fragment, is bonded to the carrier molecule using methods which are known to the skilled person, e.g. using coupling reagents. This bond should if at all possible be covalent. A suitable carrier molecule is, for example, biotinylated dextran (see Example 5) or else one of the other carrier molecules described above, in particular those like the antibody polymers described in Example 7. As in the case of the biotinylated dextran, the sites for binding the specific binding partner X or Y can be introduced before or, as described in Example 7, after the binding reaction between the analyte-specific binding partner and the carrier molecule. Several analyte-specific binding partners, rather than just one, can also be bonded to a carrier molecule. However, in addition to this preferred embodiment according to the invention, it is also possible for several carrier molecules to be bonded to one analyte-specific binding partner.

Another part of the subject-matter of this invention is a carrier molecule which is associated with, preferably covalently bonded to, one or more analyte-specific binding partners. In one embodiment of this subject-matter, the carrier molecule is a protein polymer, for example antibodies (see Example 7), albumin molecules, enzymes, or mixtures thereof, which are covalently bonded to each other, which can additionally possess binding sites, e.g. biotin, digoxigenin, fluorescein, single-stranded nucleic acid chains, dinitrophenol, etc., for a specific binding partner X or Y. The number of the binding sites should be at least 2, still better more than 5, preferably more than 10, particularly preferably more than 15, very particularly preferably more than 18, per carrier molecule, which is associated with one or more analyte-specific binding partners. In this embodiment according to the invention, the analyte-specific binding partner is preferably an antibody or an antibody fragment, an antigen, a hapten or a nucleic acid chain.

The use of the above-described carrier molecule, which is associated with one or more analyte-specific binding partners, in a homogeneous or heterogeneous binding test for the purpose of quantitatively or qualitatively detecting an analyte in a sample, in particular in a homogeneous or heterogeneous immunoassay, is also in accordance with the invention.

In that which follows, analyte-specific binding partners which are associated with the carrier molecules according to the invention are also termed conjugates. These conjugates can naturally also be used advantageously in heterogeneous binding tests as well as in homogeneous binding tests.

A conjugate according to the invention consists of a carrier molecule which is associated with one or more analyte-specific binding partners, with this conjugate possessing additional binding sites for a specific binding partner X or Y. In a special embodiment of a conjugate, the carrier molecule consists of dextran, cyclodextrin or dendrimers or of antibodies which are bonded together, albumin molecules which are bonded together, enzymes which are bonded together, or mixtures thereof which are bonded together. Their bond should preferably be covalent. The additional binding sites possessed by the conjugate according to the invention can be biotin, digoxigenin, fluorescein, dinitrophenol or single-stranded nucleic acid chains. In a particularly preferred embodiment of the conjugate according to the invention, the carrier molecule is covalently bonded to one or more analyte-specific binding partners. The conjugate according to the invention should possess at least 2, preferably more than 5, particularly preferably more than 10, very particularly preferably more than 15 and optimally more than 18 additional binding sites for the specific binding partner X or Y. Very particular preference is given to a conjugate in which the carrier molecule consists of antibodies, preferably mouse or goat IgG antibodies, which are covalently bonded together. The invention also relates to a reagent which contains one or more of these conjugates and to a test kit which contains such a reagent.

The conjugates according to the invention can be used in a homogeneous or heterogeneous binding test (e.g. an immunoassay) for the purpose of quantitatively or qualitatively detecting an analyte in a sample. In one embodiment of a binding test according to the invention, in particular a homogeneous binding test, a conjugate according to the invention which possesses specific binding sites for the specific binding partner X, which is associated with a component of a signal-generating system, is used for the purpose of quantitatively or qualitatively detecting an analyte in a sample. In another embodiment, a further conjugate according to the invention which possesses specific binding sites for the specific binding partner Y, which is associated with a component of a signal-generating system, is additionally used for the purpose of quantitatively or qualitatively detecting an analyte in a sample. The number of binding sites for the specific binding partner X or Y should be at least 2, preferably at least 5, particularly preferably at least 10 and very particularly preferably at least 15. X and Y can be one and the same specific binding partner or different specific binding partners. Avidin, streptavidin, an anti-digoxigenin antibody, an anti-dinitrophenol antibody, a single-stranded nucleic acid chain, an anti-hapten antibody, an enzyme, an enzyme substrate or an antibody which is able to bind particular polypeptides, oligopeptides or enzymes specifically are preferably used as binding partners X or Y. Within the meaning of this invention, very particular preference is given to a binding test, preferably a homogeneous binding test, which uses one or more of the conjugates according to the invention, with components of the signal-generating system being brought, as a result of the binding of the analyte-specific binding partners, to a distance from each other which permits an interaction, in particular an energy transfer, between these components, and the magnitude of this interaction being measured, or with components of the signal-generating system being brought, as a result of the binding of the analyte-specific binding partners, to a distance from each other which permits no interaction, or only very slight interaction, in particular no energy transfer or only very slight energy transfer, between these components, and the residual magnitude of this interaction being measured. In such a test, microparticles, in particular latex particles, are preferably used as components of the signal-generating system. Very particular preference is given to using microparticle-associated photosensitizers and microparticle-associated chemiluminescent substances as components of the signal-generating system in such a test method.

It is possible to use microparticles, in particular latex particles, as components of the signal-generating system in the novel methods. Microparticle-associated sensitizers, in particular photosensitizers, and microparticle-associated chemiluminescent substances are very particularly preferred as components of the signal-generating system.

Consequently, a microparticle, in particular a latex particle, to which a conjugate according to the invention is bonded by way of a specific binding partner X or Y which is bonded to the microparticle, and the use of this microparticle in a novel method, is another part of the subject-matter of this invention. In this connection, preference is given to a microparticle which, as component of a signal-generating system, is associated with photosensitizers or with chemiluminescent substances.

A test based on the LOCI method, which is described in detail in EP-0 515 194, is a particularly preferred embodiment, according to the invention, of the novel method. This test is based on using photosensitizers and what are termed acceptors as signal-generating components. On being exposed to light, the photosensitizers generate singlet oxygen which reacts with the acceptors, which are chemiluminescent components. The activated chemiluminescent component produces light, which is measured. This preferred method will be explained in more detail on the basis of a sandwich assay according to the invention: the analyte is, for example, bound to an analyte-specific binding partner R1 which can be associated with a carrier molecule which is bound, by means of the specific binding partner X, to what are termed sensitizer particles. In the excited state, the sensitizer molecules which are associated with the sensitizer particle can generate singlet oxygen. This singlet oxygen can react with the chemiluminescent compounds which are associated with what are termed chemiluminescer particles, with the metastable compound which has been formed decomposing once again with the generation of a light flash. The analyte-specific binding partner R2, which can be associated with a carrier molecule, is bound to the chemiluminescer particles by means of the specific binding partner Y. Since singlet oxygen is only stable for a short period in aqueous solutions, the chemiluminescer particles which are associated with analyte-specific binding partner and which, as a result of the formation of a sandwich complex, have arrived in the immediate vicinity of the sensitizer particles, which have been stimulated by light, for example, are stimulated to emit light. The wavelength of the emitted light, which is to be measured, can be altered using appropriate fluorescent dyes in the chemiluminescer particles. In this method, the sample is preferably initially incubated with the analyte-specific binding partners R1 and R2, after which the specific binding partners X and Y, which are associated with the sensitizer particles and chemiluminescer particles, respectively, are added.

Other energy transfer methods, which could also be used in the novel method, are based on energy transfer in accordance with Förster (Mathis, G. (1993) Clin. Chem. 39: 1953-1959; U.S. Pat. No. 5,527,684) or on the use of photosensitizers and fluorophores (WO 95/06877) or on the combination of radioactive irradiation and fluorophores (S. Udenfriend et al. (1985) Proc. Math. Acad. Sci. 82: 8672-8676) or on using suitable enzyme cascades (U.S. Pat. No. 4,663,278).

In another embodiment of the novel method, the analyte-specific binding partner R1 is associated with a component of a signal-generating system and the analyte-specific binding partner R2 possesses specific binding sites for the specific binding partner Y, which is associated with a component of a signal-generating system, with R2 possessing more than one binding site for the given specific binding partner Y which is associated with components of a signal-generating system.

This invention also relates to a reagent, in liquid or lyophilized form, which contains one or more of the above-described carrier molecules according to the invention, which carrier molecules are in each case associated with one or more analyte-specific binding partners, or contains the microparticles according to the invention. This invention also encompasses a test kit which contains such a reagent. This also applies to the use of this reagent and/or the test kit for implementing a homogeneous or heterogeneous binding test for the purpose of quantitatively or qualitatively detecting an analyte in a sample, preferably for implementing one of the homogeneous methods described in the patent claims.

The invention also relates to a test kit for implementing the homogeneous binding test according to the invention. This test kit is characterized by the fact that it contains an analyte-specific binding partner R1 which possesses more than one specific binding site for the specific binding partner X, which is associated with a component of a signal-generating system, and by the fact that this test kit contains an analyte-specific binding partner R2 which possesses more than one specific binding site for the specific binding partner Y, which is associated with a component of a signal-generating system.

The test kit according to the invention can also additionally contain the specific binding partner(s) X and/or Y which is/are associated with components of a signal-generating system. In addition, the test kits according to the invention can also contain a pack information leaflet, dilution buffers, standards, controls, system reagents and/or other reagents and materials (e.g. cuvettes and sample withdrawal instruments) which are required for implementing the tests.

The test kits according to the invention preferably contain an analyte-specific binding partner R1 which consists of one or more analyte-specific binding partner(s), which is/are associated with biotinylated dextran, biotinylated protein polymers, biotinylated antibody polymers or another carrier molecule, and/or an analyte-specific binding partner R2 which consists of one or more analyte-specific binding partner(s) which is/are associated with biotinylated dextran, biotinylated protein polymers, biotinylated antibody polymers or another carrier molecule.

The examples which are described below serve to illustrate individual aspects of this invention and are not to be understood as representing any restriction.

EXAMPLES

Example 1

Preparing Sensitizer Particles or Chemiluminescer Particles

The preparation of sensitizer particles and chemiluminescer particles is described in detail in EP 0 515 194, Clin. Chem. (1996) 42: 1518-1526 and Proc. Natl. Acad. Sci. (1994) 91: 5426-5430. The particles can, for example, carry dextran envelopes and additionally possess bound streptavidin (see also Proc. Natl. Acad. Sci. (1994) 91: 5426-5430). The preparation of a variant of sensitizer particles and chemiluminescer particles is described below by way of example (see also EP 0 515 194, Example 8, for further details):

Preparing Sensitizer Particles:

A solution of chlorophyll-a in benzyl alcohol (1.0 ml; 0.6 mM) is added to 8.0 ml of benzyl alcohol which had been heated to 105° C. A suspension of latex beads (175 nm, carboxyl-modified latex, Bangs Laboratories, Carmel, Ind.) in water (10%; 1.0 ml) is added to the benzyl alcohol solution. The mixture is stirred at 105° C. for 5 minutes and then cooled down to room temperature. 10 ml of ethanol are added and the mixture is centrifuged. The pellet is resuspended in a 1:1 water-ethanol mixture (10 ml) and the suspension is centrifuged once again. The same procedure is repeated with water and the pellet is subsequently taken up in physiological sodium chloride solution.

Preparing the Chemiluminescer Particles (=Acceptor Particles):

20 ml of the carboxyl-modified latex particle suspension (10% suspension in water) are mixed with 20 ml of 2-ethoxyethanol. The mixture is heated to 90° C. 20 ml of a solution composed of 10 mM dioxene, 20 mM europium chelate with the agent 3-(2-thienoyl)-1,1,1-trifluoroacetone (Kodak, CAS #14054-87-6) (EuTTA) and 60 mM trioctylphosphine oxide (TOPO) in 2-ethoxyethanol are added to the particle suspension. The mixture is heated further at 97° C. for 7 minutes. After it has been cooled down to room temperature, 40 ml of ethanol are added and the mixture is centrifuged. The pellet is then resuspended in 80% ethanol and centrifuged. This washing process is repeated with 10% ethanol. In conclusion, the particles are taken up in physiological sodium chloride solution.

Example 2

Preparing Universal Reagents

Chemiluminescer Particles (=Acceptor Particles) Containing Streptavidin:

20 mg of acceptor particles were mixed together with 2.0 mg of streptavidin (from Gerbu, high purity, #3058) and 0.2 mg of sodium cyanoborohydride (from Sigma, S 8628) in a coupling buffer (0.05 M β-morpholinoethanesulfonic acid; from Serva, Art. 29834) and the mixture was incubated at +37° C. for 24 hours. The coupling conditions during the incubation were: 50 mg of particles/ml of coupling, 0.5 mg of sodium cyano-borohydride/ml of coupling, 2 mg of streptavidin/20 mg of particles.

After the incubation, 65.6 μl of a 0.48 M solution of carboxymethoxylamine hemihydrochloride (from Aldrich, 98% strength, Cat. No. C1,340-8) were added and mixed in and the mixture was incubated at +37° C. for a further 2 hours.

The supernatant was separated off by centrifugation and the particles were resuspended in coupling buffer (containing 0.6 M NaCl, from Merck). After that, the supernatant was once again separated off by centrifugation and the particles were taken up and resuspended in storage buffer (0.1 M tris-HCl, 0.3 M NaCl, 25 mM EDTA, 0.1% BSA, 0.1% dextran T-500, 0.1% zwittergent 3-14, 0.01% gentamycin, 15 ppm of ProClin-300, pH 8.0).

Sensitizer Particles Containing Streptavidin:

Sensitizer particles were coupled in analogy with the "chemiluminescer particles (=acceptor particles) containing streptavidin" coupling.

Sensitizer Particles Containing Anti-Digoxigenin:

15 mg of sensitizer particles were mixed together with 3 mg of anti-digoxigenin antibody (Mab DIG 2H6, from Dade Behring Inc.) and 0.15 mg of sodium cyanoboro-hydride (from Sigma, S 8628) in a coupling buffer (0.05 M β-morpholinoethanesulfonic acid; from Serva, Art. 29834), and the mixture was incubated at +37° C. for 24 hours. The coupling conditions during the incubation were: 32.8 mg of particles/ml of coupling, 6.6 mg of antibody/ml of coupling, 0.33 mg of sodium cyano-borohydride/ml of coupling, 3 mg of antibody/15 mg of particles.

After the incubation, 49.2 μl of an 0.48 M solution of carboxymethylamine hemihydrochloride (from Aldrich, 98% strength, Cat. No. C1,340-8) were added and mixed in and the mixture was incubated at +37° C. for a further 2 hours.

The supernatant was separated off by centrifugation and the particles were resuspended in coupling buffer (containing 0.6 M NaCl, from Merck). After that, the supernatant was once again separated off by centrifugation and the particles were taken up and resuspended in storage buffer (0.1 M tris-HCl, 0.3 M NaCl, 25 mM EDTA, 0.1% BSA, 0.1% dextran T-500, 0.1% zwittergent 3-14, 0.01% gentamycin, 15 ppm of ProClin-300, pH 8.0).

Chemiluminescer Particles (=Acceptor Particles) Containing Anti-Digoxigenin or Anti-Troponin:

Acceptor particles were coupled to antibody directed against digoxigenin or against troponin in analogy with the "sensitizer particles containing anti-digoxigenin" coupling.

In the following examples, universal reagent A (acceptor particles containing streptavidin) is used in combination with universal reagent B (sensitizer particles containing anti-digoxigenin), or universal reagent A (acceptor particles containing anti-digoxigenin) is used in combination with universal reagent B (sensitizer particles containing streptavidin).

Example 3

PSA Assay

Preparing PSA Specific Reagents
Conjugate C1 (Biotinylated Anti-PSA Antibody):

0.23 mg of biotin-LC-NHS (from Pierce, Art. 21336, Immuno Pure), dissolved in DMSO (from RdH, 34943), was added to 2.3 mg of anti-PSA antibody (MAK <PSA> 92-284/03, Dade Behring Marburg GmbH, in 0.1 M sodium carbonate (from RdH, 31432)) and mixed in, and the mixture was incubated at +4° C. for 16 hours. Molar ratio [Ab]: [biotin-LC-NHS] employed=1:35.

The conjugate was purified through a PD-10 Sephadex G-25M (from Pharmacia Biotech, Code 17-0851-01) column using phosphate buffer (0.05 M sodium dihydrogen phosphate containing 0.15 M sodium chloride, pH 7.5).

Conjugate C2 (Digoxigenin-Labeled Anti-PSA Antibody):

The anti-PSA antibody (MAK <PSA> 92-283/029 Dade Behring Marburg GmbH) was labeled with digoxigenin in accordance with the DIG-antibody labeling kit (from Boehringer Mannheim Biochemica, Order No. 1367200, implementation: protein labeling with DIG-NHS 1. monoclonal antibodies) directions/instructions for use.

Assay Buffer 0.1 mol of tris/l plus 0.3 mol of NaCl/l plus 25 mmol of EDTA/l plus 0.1% RSA plus 0.1% dextran T-500 plus 0.1% zwittergent 3-14 plus 0.01% gentamycin plus 15 ppm of ProClin-300, pH 8.00.

Implementing a PSA Assay

In order to carry out the test, the components were mixed and incubated as follows:

| | |
|---|---|
| 10 µl | of sample |
| 75 µl | of assay buffer |
| 25 µl | of conjugate C1 (biotinylated anti-PSA antibody) and conjugate C2 (digoxigeninated anti-PSA antibody), in each case 0.96 µg/ml |
| 371 | seconds of incubation at +37° C. |
| 100 µl | of assay buffer |
| 20 µl | of sensitizer particles containing anti-digoxigenin (0.2 mg/ml) |
| 20 µl | of acceptor particles containing streptavidin (0.2 mg/ml) |
| 762.5 | seconds of incubation at +37° C. |

Measurement

The test was carried out and measured on a modified Tecan Sample Processor, see Ullman et al. (Clinical Chemistry 42: 1518-1526, 1996, EP 0515194 A2), and the signals were recorded.

Results

TABLE 1

Standard curve in the PSA assay:

| PSA standard No. | ng/ml | Signal [counts] |
|---|---|---|
| 1 | 0 | 2810 |
| 2 | 0.1 | 3031 |
| 3 | 0.3 | 3679 |
| 4 | 0.9 | 4611 |
| 5 | 3.9 | 10316 |
| 6 | 10 | 24178 |
| 7 | 34.8 | 114241 |
| 8 | 79.4 | 326876 |
| 9 | 270 | 856074 |

TABLE 2

Samples which were measured using the PSA assay according to the invention:

| Sample ID (PSA sera) | PSA assay Signal [counts] | PSA assay PSA concentration [ng/ml] | Reference test: Abbott-IMx total PSA PSA concentration [ng/ml] |
|---|---|---|---|
| OF 22 | 6171.5 | 2.2 | 2.02 |
| OF 23 | 5204.0 | 1.5 | 1.11 |
| OF 24 | 10443.0 | 4.4 | 3.65 |

TABLE 2-continued

Samples which were measured using the PSA assay according to the invention:

| Sample ID (PSA sera) | PSA assay Signal [counts] | PSA assay PSA concentration [ng/ml] | Reference test: Abbott-IMx total PSA PSA concentration [ng/ml] |
|---|---|---|---|
| OF 25 | 3301.0 | 0.1 | 0.22 |
| OF 27 | 35440.0 | 13.7 | 12.41 |
| OF 28 | 12248.5 | 5.2 | 4.79 |
| OF 29 | 28453.0 | 11.4 | 9.94 |
| OF 30 | 95165.5 | 30.2 | 29.26 |
| OF 31 | 5012.0 | 1.4 | 1.09 |
| OF 32 | 12934.5 | 5.5 | 5.37 |
| OF 33 | 4959.0 | 1.4 | 1.00 |
| OF 35 | 50551.5 | 18.3 | 18.15 |
| OF 40 | 4737.0 | 1.2 | 0.61 |
| OF 45 | 4196.0 | 0.8 | 0.48 |
| OF 50 | 22371.0 | 9.2 | 9.89 |
| OF 55 | 3989.5 | 0.7 | 0.67 |
| OF 60 | 5869.5 | 2.0 | 1.86 |

The above table shows that the values determined in the novel method agreed, within normal limits, with those in the comparison method (Abbott IMx total PSA, list 5 No. 1D85). This verifies that the method according to the invention functions.

Example 4

Varying the Number of Biotin Labels Per Antibody

The anti-PSA antibody (Mab<PSA>92-284/03, Dade Behring Marburg GmbH) was conjugated with varying quantities of biotin molecules, and the anti-PSA antibody (Mab<PSA>92-283/09, Dade Behring Marburg GmbH) was conjugated with varying quantities of digoxigenin molecules, in accordance with the biotinylation method described in Example 3. The results obtained with the antibody pairs are shown in the following table.

TABLE 3

PSA assay based on antibodies having differing numbers of binding sites for the specific binding partners X and Y. Measurement signal given in counts.

| Calibrator nominal value [ng/ml] | 1 biotin or digoxigenin per antibody [counts] | 2 biotin or digoxigenin molecules per antibody [counts] | 3 biotin or digoxigenin molecules per antibody [counts] | 5 biotin or digoxigenin molecules per antibody [counts] |
|---|---|---|---|---|
| 0 | 2674 | 2600 | 2461 | 2542 |
| 0.1 | 8622 | 7055 | 6019 | 4704 |
| 0.3 | 13080 | 11492 | 9839 | 8334 |
| 1.0 | 18442 | 21248 | 21599 | 21963 |
| 3.0 | 31959 | 52192 | 62751 | 71571 |
| 10.0 | 101813 | 191158 | 251553 | 278551 |
| 30.0 | 345151 | 656275 | 812705 | 953906 |
| 50.0 | 578619 | 1016250 | 1227390 | 1438690 |
| 100.0 | 1258490 | 1983200 | 2339990 | 2593270 |

Example 5

Preparing Dextran-Antibody-Biotin Conjugates

Activating Antibodies with N-succinimidyl S-acetylthio-acetate (SATA)

10.4 mg of anti-PSA antibody (Mab<PSA>92-284/03, Dade Behring Marburg GmbH) in 0.1 M sodium carbonate buffer (from Riedel de Haen, 31432) are rebuffered in mixed buffer (LiBO$_3$/20% dioxane)., pH 8.5, and mixed with 104 μl of SATA (from Pierce) in DMF (2 mg/ml). After the mixture had been incubated at 37° C. for 1.5 hours, it is incubated for 45 minutes with 200 μl of NH$_2$OH.

The conjugate is then desalted through a PD-10 column using 0.1 M phosphate buffer, pH 6.0.

Preparing Activated Biotin-Dextran 3.9 mg (1.95 ml) of FlukaBioDex (70000 kDa, product number 14402, biotin substitution 20 mol/mol) are taken up in mixed buffer (2 mg/ml) and mixed with 26 μl of GMBS solution (N-maleimidobutyryloxysuccinimide ester, from Pierce) in dioxane (6 mg/ml). This mixture is incubated at 18° C. for 1 hour. The conjugate is then desalted through a PD-10 column using 0.1 M phosphate buffer, pH 6.0.

Coupling the Activated Antibody to the Activated Biotin-Dextran

Conjugate 1:

1.7 ml of the antibody-SATA solution (1 mg/ml) are mixed with 509 μl of the FlukaBioDex-GMBS solution (1.32 mg/ml). This mixture is incubated at 37° C. for 2 hours and then stopped with 220 μl of an 0.1 M solution of n-ethylmaleimide. The purification/desalting takes place through Sephacryl S300 (diameter 1.6 cm, gel bed height 90 cm, quantity loaded approx. 2 ml) using 0.1 M TRIS/HCl, 150 mM NaCl, pH 7.4. The fractions containing the conjugate were pooled and concentrated down to 1.7 ml (≈0.65 mg/ml).

Conjugate 2:

1.7 ml of the antibody-SATA solution (1 mg/ml) are mixed with 102 μl of the FlukaBioDex-GMBS solution (1.32 mg/ml). This mixture is incubated at 37° C. for 2 hours and then stopped with 180 μl of an 0.1 M solution of n-ethylmaleimide. The purification/desalting takes place through Fluka Sephacryl S300 (diameter 1.6 cm, gel bed height 90 cm, quantity loaded approx. 2 ml) using 0.1 M TRIS/HCl, 150 mM NaCl, pH 7.4. The fractions containing the conjugate were pooled and concentrated down to 1.7 ml (≈0.64 mg/ml).

Because of the different formulations, a ratio of approx. 18 biotin molecules per antibody was obtained for conjugate 1 and a ratio of approx. 3 biotin molecules per antibody is obtained for conjugate 2.

These conjugates were used in the above-described PSA assay in combination with the above-described digoxigeninated anti-PSA antibodies having increasing antibody/digoxigenin ratios. The concentration of the dextran conjugates was 9.75 μg/ml and the digoxigeninated anti-PSA antibodies were used at a concentration of 8.8 μg/ml. The results are shown in the following table.

TABLE 4

PSA assay using dextran-antibody-biotin conjugates. Measurement signal given in counts.

| Calibrator nominal value [ng/ml] | Conjugate 1 (18 biotin molecules per antibody) in combination with digoxigeninated anti-PSA antibody (Ab/Dig 1:1) [counts] | Conjugate 1 (18 biotin molecules per antibody) in combination with digoxigeninated anti-PSA antibody (Ab/Dig 1:5) [counts] | Conjugate 2 (3 biotin molecules per antibody) in combination with digoxigeninated anti-PSA antibody (Ab/Dig 1:1) [counts] | Conjugate 2 (3 biotin molecules per antibody) in combination with digoxigeninated anti-PSA antibody (Ab/Dig 1:5) [counts] |
|---|---|---|---|---|
| 0 | 4309 | 4157 | 4937 | 4981 |
| 0.1 | 6745 | 11647 | 5826 | 7613 |
| 0.3 | 11837 | 27686 | 7817 | 13416 |
| 1.0 | 32488 | 84783 | 15512 | 33460 |
| 3.0 | 116736 | 287554 | 44103 | 98896 |
| 10.0 | 469406 | 1108220 | 152400 | 375343 |
| 30.0 | 1655420 | 3176980 | 1060780 | 1259030 |
| 50.0 | 2712870 | 4573200 | 2501150 | 2076760 |
| 100.0 | 4957770 | 7049890 | 2339990 | 4166780 |

Example 6

Rubella IgM Assay

Preparing Rubella IgM-Specific Reagents

Conjugate C1 (Biotinylated Anti-Human IgM Antibody):

Goat anti-human IgM antibody (Pab <h-IgM> 62FX022, Dade Behring Marburg GmbH) was biotinylated in analogy with the biotinylation of the anti-PSA antibodies (see Example 3).

Conjugate C2 (Digoxigenin-Labeled Anti-Rubella Antibody):

The anti-rubella antibody (Mab <rubella> 93-9/08, Dade Behring Marburg GmbH) was labeled with digoxigenin in accordance with the DIG-antibody labeling kit (from Boehringer Mannheim Biochemica, order No. 1367200, implementation: protein labeling using DIG-NHS 1. monoclonal antibodies) directions/instructions for use.

Assay Buffer:

0.1 mol of tris/l plus 0.3 mol of NaCl/l plus 25 mmol of EDTA/l plus 0.1% RSA plus 0.1% dextran T-500 plus 0.1% zwittergent 3-14 plus 0.01% gentamycin plus 15 ppm of ProClin-300, pH 7.3.

Rheumatoid Factor (RF) Absorbent:

Rheumatoid factor (RF) absorbent from Dade Behring Marburg GmbH, product number OUCG.

Rubella Antigen:

From Intergen, CDP (lot 8320)

Implementing a Rubella IgM Assay

In order to carry out the test, the components were mixed and incubated as follows:

| | |
|---|---|
| 10 µl | of sample, diluted 1 + 9 parts in RF absorbent |
| 40 µl | of assay buffer |
| 25 µl | of conjugate C1 (biotinylated anti-human IgM antibody, 8 µg/ml) and conjugate C2 (digoxigeninated anti-rubella antibody, 2 µg/ml) |
| 25 µl | of rubella antigen (4 [µg/ml]) |
| 453.5 | seconds of incubation at +37° C. |
| 75 µl | of assay buffer |
| 25 µl | of acceptor particles containing anti-digoxigenin (0.05 mg/ml) |
| 50 µl | of sensitizer particle containing streptavidin (0.4 mg/ml) |
| 432.5 | seconds of incubation at +37° C. |

Measurement

The test was carried out and measured on a modified Tecan Sample Processor, see Ullman et al. (Clinical Chemistry 42: 1518-1526, 1996, EP 0515 194 A2), and the signals were recorded.

Result of a Rubella IgM Assay

TABLE 5

Measuring samples in the rubella IgM assay. The measurement signal is given in counts or in mE (extinction measurement).

| Sample ID | Rubella IgM [counts] | DiaSorin reference test [mE] | DiaSorin assessment |
|---|---|---|---|
| 665550 | 4383 | 101 | negative |
| NS24 | 13477 | 452 | borderline |
| 6DD416 | 22371 | 1825 | positive |
| 35-033 | 131152 | >measurement range | positive |

As is evident from the above table, the results which were obtained using the method according to the invention agree, within normal limits, with those obtained in the comparison method (DiaSorin, ETI-RUBEK-M reverse, P2471). This verifies that the method according to the invention also functions in an indirect test procedure.

Example 7

Using a Troponin Assay to Compare a Biotin Standard Conjugate with a Biotinylated Carrier Molecule-Fab' Conjugate Preparing a Biotinylated Carrier Molecule-Fab' Conjugate ("M-IgG-Biotin Anti-Troponin Conjugate"):

A solution of murine IgG antibodies ("M-IgG") (15.0 ml, 2.6 mg of M-IgG/ml, 0.26 mmol) in 0.1 M phosphate buffer (5 mM EDTA, pH 7.0) is mixed with an aqueous solution of sulfosuccinimidyl (4-iodoacetyl)amino-benzoate (0.66 ml, 2.0 mg/ml). After a reaction time of 1 hour at 25° C., the mixture is concentrated using a gel filtration column (AcA22, Ciphergen, Fermont, Calif.), and purified. The fractions containing the monomeric, activated M-IgG (HPLC-tested) are pooled.

A solution (3.0 ml, 10 mg/ml) of an F(ab')$_2$ fragment of an anti-troponin antibody in an 0.1 M phosphate buffer (5 mM EDTA, pH 6.0) is mixed with 0.091 ml of a mixture of dithiothreitol (15.4 mg/ml) and 2-mercaptoethanol (15.6 µl/ml). After a reaction time of 1 hour at 37° C., the mixture was concentrated using a gel filtration column (AcA22, Ciphergen, Fermont, Calif.), and purified. The fractions containing the Fab' antibody fragment are pooled.

A mixture of the activated M-IgG (20.5 mg; 0.14 mmol) and the Fab' fragment (20.5 mg; 0.41 mmol) is rebuffered into a phosphate buffer pH 7.0 (5 mM EDTA) using an Amicon ultrafiltration cell. The mixture is concentrated down to 5.0 mg of protein/ml and incubated at 2-8° C. for 24-70 hours. After that, an aqueous solution of N-ethylmaleimide (20 mg/ml; 50 µl per ml of protein solution) is added. After one hour at room temperature, the solution is concentrated in 10 mM phosphate buffer (300 mM NaCl, pH 7.0) using a gel filtration column (AcA22, Ciphergen, Fermont, Calif.), and purified. The protein fractions are pooled.

An aqueous solution of NHS-PEO4-Biotin (Pierce Chemical Company, Rockford, Ill.; 0.095 ml, 0.5 mg/ml) is added to the Fab'-M-IgG conjugate in the pH 7.0 phosphate buffer (6 ml; 0.8 mg/ml; 16 µmol). After a reaction time of 4 hours at room temperature, the mixture is diafiltered against the pH 7.0 phosphate buffer.

Preparing an Fab'-Biotin Conjugate ("Standard Biotin Anti-Troponin Conjugate")

A solution of the Fab' fragment of the anti-troponin antibody (2 ml of a 5 mg/ml protein solution) in 10 mM phosphate buffer (300 mM NaCl, pH 7.0) is mixed with 0.22 ml of a PEO-iodoacetylbiotin solution (10 mg/ml; 4 mmol in DMF) from Pierce Chemical Company, Rockford, Ill. After a reaction time of 4 hours at room temperature, the mixture is diafiltered against the pH 7.0 phosphate buffer. The protein concentration was determined using the BCA protein assay supplied by Pierce Chemical Company.

Troponin Immunoassays

A) Test Implementation

In order to carry out the test, the components were mixed and incubated as follows:

| | |
|---|---|
| 20 µl | of sample |
| 10 µl | of water |
| 15 µl | of conjugate (standard biotin anti-troponin conjugate: 12.5 µg/ml or M-IgG-biotin anti-troponin conjugate: 8 µg/ml) |
| 13 µl | of acceptor particles containing anti-troponin antibody (210 µg/ml) |
| 435 | seconds of incubation at +37° C. |
| 13 µl | of sensitizer particles containing streptavidin (1.5 mg/ml) |
| 10 µl | of water |
| 87 | seconds of incubation at +37° C. |
| 169 µl | of water |

Measurement

The test was carried out and measured on a modified Tecan Sample Processor, see Ullman et al. (Clinical Chemistry 42: 1518-1526, 1996, EP 0515194 A2), and the signals were recorded.

B) Results

TABLE 6

Troponin immunoassay using two different anti-troponin conjugates. Measurement signal given in counts.

| Troponin calibrator nominal value [ng/ml] | Standard biotin anti-troponin conjugate [counts] | M-IgG-biotin anti-troponin conjugate [counts] |
|---|---|---|
| 0 | 5236 | 4337 |
| 0.025 | 6008 | 7475 |
| 0.05 | 6980 | 10684 |
| 0.1 | 8744 | 17421 |
| 0.5 | 22752 | 73511 |
| 2.25 | 91614 | 362965 |

The biotinylated carrier molecule-Fab' conjugate (=M-IgG-biotin anti-troponin conjugate) gives a much steeper calibration curve, thereby imparting greater precision to the test.

The invention claimed is:

1. A homogeneous method for quantitatively or qualitatively detecting an analyte in a sample (sample analyte) comprising
   (1) contacting the sample with
      (a) a first conjugate molecule comprising an analyte-specific binding partner R1 and possessing specific binding sites for a specific binding partner X, wherein R1 is capable of binding to the analyte or to an analyte-specific binding partner R2;
      (b) a second conjugate molecule comprising an analyte-specific binding partner R2 and possessing specific binding sites for a specific binding partner Y, wherein R2 is capable of binding to the analyte or to R1;
      (c) the specific binding partner X, which is associated with a first component of a signal-generating system; and
      (d) the specific binding partner Y, which is associated with a second component of the signal-generating system;
   wherein at least one of the conjugates comprising R1 or R2 possesses more than one binding site for the respective specific binding partner X or Y;
   wherein the first and second components of the signal-generating system enter into a detectable interaction when spatially close to each other and the detectable interaction comprises a direct energy transfer between the components;
   wherein (i) both R1 and R2 are able to bind specifically to the sample analyte, or (ii) only R1 is able to bind specifically to the sample analyte and R2 can compete with the sample analyte in binding to R1; and
   (2) detecting the analyte in the sample (sample analyte) by measuring the magnitude of the interaction between the components of the signal-generating system;
   wherein said method is a homogeneous binding test.

2. The method of claim 1, wherein R1 is bound to the component of the signal-generating system by way of X during or after the binding reaction with the analyte.

3. The method of claim 1, wherein the number of binding sites possessed by the conjugate comprising R1 for the specific binding partner X is at least 2.

4. The method of claim 1, wherein the number of binding sites possessed by the conjugate comprising R2 for the specific binding partner Y is at least 2.

5. The method of claim 1, wherein R1 and R2 are the same analyte-specific binding partner.

6. The method of claim 1, wherein R1 and R2 are able to bind specifically to the sample analyte.

7. The method of claim 1, wherein the binding sites possessed by the conjugate comprising R1 for the specific binding partner X are chosen from hapten, antigen, biotin, digoxigenin, fluorescein, single-stranded nucleic acid chain, and dinitrophenol.

8. The method of claim 1, wherein the binding sites possessed by the conjugate comprising R2 for the specific binding partner Y are chosen from hapten, antigen, biotin, digoxigenin, fluorescein, single-stranded nucleic acid chain, and dinitrophenol.

9. The method of claim 1, wherein X and Y are the same specific binding partner.

10. The method of claim 1, wherein X is avidin, streptavidin, an anti-digoxigenin antibody, an anti-dinitrophenol antibody, a single-stranded nucleic acid chain, an anti-hapten antibody, an enzyme, or an enzyme substrate, or an antibody which specifically binds to a peptide antigen.

11. The method of claim 1, wherein Y is avidin, streptavidin, an anti-digoxigenin antibody, an anti-dinitrophenol antibody, a single-stranded nucleic acid chain, an anti-hapten antibody, an enzyme, or an enzyme substrate, or an antibody which specifically binds to a peptide antigen.

12. The method of claim 1, wherein the components of the signal-generating system are brought to a distance from each other which permits a detectable interaction between these components, as a result of the analyte being bound to at least one of R1 and R2.

13. The method of claim 1, wherein the components of the signal-generating system are not brought to a distance from each other which permits a detectable interaction between these components, as a result of R1 being bound by sample analyte in competition with R2.

14. The method of claim 1, wherein the components of the signal-generating system are microparticles associated with photosensitizers or microparticles associated with chemiluminescent substances.

15. The method of claim 1, wherein R2 is bound to components of the signal-generating system by way of Y during or after the binding reaction with the analyte.

16. The method of claim 3, wherein the number of binding sites possessed by the conjugate comprising R1 for the specific binding partner X is at least 5.

17. The method of claim 3, wherein the number of binding sites possessed by the conjugate comprising R1 for the specific binding partner X is at least 10.

18. The method of claim 3, wherein the number of binding sites possessed by the conjugate comprising R1 for the specific binding partner X is at least 15.

19. The method of claim 4, wherein the number of binding sites possessed by the conjugate comprising R2 for the specific binding partner Y is at least 5.

20. The method of claim 4, wherein the number of binding sites possessed by the conjugate comprising R2 for the specific binding partner Y is at least 10.

21. The method of claim 4, wherein the number of binding sites possessed by the conjugate comprising R2 for the specific binding partner Y is at least 15.

22. The method of claim 14, wherein the microparticles are latex particles.

23. The method of claim 1, wherein the first component of the signal-generating system is an energy donor and the second component of the signal-generating system is an energy recipient.

24. The method of claim 1, wherein one component of the signal-generating system is a photosensitizer.

25. The method of claim 1, wherein at least one component of the signal-generating system is a fluorophore.

26. The method of claim 1, wherein at least one of the analyte-specific binding partners R1 and R2 is an antibody.

27. The method of claim 1, wherein both analyte-specific binding partners R1 and R2 are antibodies.

28. The method of claim 1, wherein the first and second conjugates further comprise a carrier molecule to which are bound the analyte-specific binding partners R1 and R2 and the specific binding sites for the specific binding partners X and Y.

29. The method of claim 1, wherein the specific binding partners X and Y are bound to microparticles that also comprise the components of the signal-generating system.

* * * * *

UNITED STATES PATENT AND TRADEMARK OFFICE
CERTIFICATE OF CORRECTION

| | |
|---|---|
| PATENT NO. | : 8,399,209 B2 |
| APPLICATION NO. | : 11/443270 |
| DATED | : March 19, 2013 |
| INVENTOR(S) | : Schelp et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 647 days.

Signed and Sealed this
Tenth Day of February, 2015

Michelle K. Lee
*Deputy Director of the United States Patent and Trademark Office*